United States Patent
Ravikumar et al.

(10) Patent No.: US 11,627,984 B2
(45) Date of Patent: Apr. 18, 2023

(54) EXCHANGER SURGICAL ACCESS PORT AND METHODS OF USE

(71) Applicant: TELEFLEX MEDICAL INCORPORATED, Morrisville, NC (US)

(72) Inventors: Sundaram Ravikumar, Briarcliff Manor, NY (US); Harry Allan Alward, Shelton, CT (US); Guy Osborne, Trumbull, CT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 827 days.

(21) Appl. No.: 16/445,698

(22) Filed: Jun. 19, 2019

(65) Prior Publication Data
US 2019/0298408 A1 Oct. 3, 2019

Related U.S. Application Data

(63) Continuation of application No. 14/798,987, filed on Jul. 14, 2015, now Pat. No. 10,368,907.
(Continued)

(51) Int. Cl.
A61B 17/34 (2006.01)
A61B 17/29 (2006.01)
(Continued)

(52) U.S. Cl.
CPC .......... *A61B 17/3421* (2013.01); *A61B 17/29* (2013.01); *A61B 17/3417* (2013.01);
(Continued)

(58) Field of Classification Search
CPC .. A61M 2039/0261; A61M 2039/0279; A61M 2039/0626; A61M 25/02;
(Continued)

(56) References Cited

U.S. PATENT DOCUMENTS

| | | |
|---|---|---|
| 4,655,750 A | 4/1987 | Vaillancourt |
| 5,201,742 A | 4/1993 | Hasson |

(Continued)

FOREIGN PATENT DOCUMENTS

| | | |
|---|---|---|
| CN | 1695566 A | 11/2005 |
| CN | 101586725 A | 11/2009 |

(Continued)

*Primary Examiner* — Brandy S Lee
(74) *Attorney, Agent, or Firm* — BakerHostetler

(57) ABSTRACT

A surgical instrument access port assembly and method of use, the surgical instrument access port a surgical instrument has a needle lumen and a surgical access port. The needle lumen extends in a longitudinal direction and includes a needle tip at a distal end, and a body portion at a proximal end, the body portion having at least one recess or finger. The surgical access port has a cannula defining a hollow cannula shaft, and a tapered hub attached to a proximal end of the cannula. The tapered hub includes at least one inner ring configured to abut against the at least one recess or finger while the surgical instrument is inserted into the cannula of the surgical access port.

19 Claims, 17 Drawing Sheets

Related U.S. Application Data

(60) Provisional application No. 62/024,999, filed on Jul. 15, 2014.

(51) Int. Cl.
*A61M 39/02* (2006.01)
*A61B 17/00* (2006.01)

(52) U.S. Cl.
CPC . *A61M 39/0247* (2013.01); *A61B 2017/0042* (2013.01); *A61B 2017/00477* (2013.01); *A61B 2017/2901* (2013.01); *A61B 2017/3407* (2013.01); *A61B 2017/3492* (2013.01); *A61M 2039/027* (2013.01); *A61M 2039/0279* (2013.01); *A61M 2039/0288* (2013.01)

(58) Field of Classification Search
CPC .. A61M 2039/0273; A61M 2039/0255; A61M 2039/062; A61M 39/0247; A61M 2039/027; A61M 2039/0288; A61B 2017/3488; A61B 17/29; A61B 17/3417; A61B 17/3421; A61B 2017/0042; A61B 2017/00477; A61B 2017/2901; A61B 2017/3407; A61B 2017/3492
See application file for complete search history.

(56) References Cited

U.S. PATENT DOCUMENTS

| | | | |
|---|---|---|---|
| 5,282,800 A | 2/1994 | Foshee et al. | |
| 5,413,561 A | 5/1995 | Fischell et al. | |
| 5,454,790 A | 10/1995 | Dubrul | |
| 5,456,673 A | 10/1995 | Ziegler et al. | |
| 5,505,710 A | 4/1996 | Dorsey, III | |
| 5,626,597 A | 5/1997 | Urban et al. | |
| 5,658,272 A * | 8/1997 | Hasson | A61B 17/3403 606/1 |
| 5,759,188 A | 6/1998 | Yoon | |
| 5,868,714 A | 2/1999 | Danks | |
| 6,159,224 A | 12/2000 | Yoon | |
| 6,197,002 B1 | 3/2001 | Peterson | |
| 6,224,569 B1 | 5/2001 | Brimhall | |
| 6,336,914 B1 | 1/2002 | Gillespie, III | |
| 7,766,937 B2 | 8/2010 | Ravikumar | |
| 8,133,255 B2 | 3/2012 | Ravikumar | |
| 8,230,863 B2 | 7/2012 | Ravikumar et al. | |
| 8,313,507 B2 | 11/2012 | Ravikumar | |
| 8,956,351 B2 | 2/2015 | Ravikumar et al. | |
| 9,326,784 B2 | 5/2016 | Ravikumar | |
| 9,486,238 B2 | 11/2016 | Ravikumar | |
| 9,492,187 B2 | 11/2016 | Ravikumar et al. | |
| 10,166,038 B2 | 1/2019 | Ravikumar et al. | |
| 10,368,907 B2 | 8/2019 | Ravikumar et al. | |
| 10,390,852 B2 | 8/2019 | Ravikumar et al. | |
| 10,537,347 B2 | 1/2020 | Ravikumar et al. | |
| 2003/0130693 A1 | 7/2003 | Levin et al. | |
| 2003/0181858 A1 | 9/2003 | Lajtai et al. | |
| 2004/0111061 A1 | 6/2004 | Curran | |
| 2006/0074374 A1 | 4/2006 | Gresham | |
| 2007/0088277 A1 | 4/2007 | McGinley et al. | |
| 2007/0093755 A1 | 4/2007 | Koos et al. | |
| 2007/0093790 A1 | 4/2007 | Downey et al. | |
| 2007/0162066 A1 | 7/2007 | Lyon | |
| 2007/0250112 A1 | 10/2007 | Ravikumar et al. | |
| 2007/0282170 A1 | 12/2007 | Ravikumar | |
| 2008/0215078 A1 | 9/2008 | Bennett | |
| 2009/0247900 A1 | 10/2009 | Zimmer | |
| 2010/0016884 A1 | 1/2010 | Ravikumar | |
| 2010/0222747 A1 | 9/2010 | Wenchell et al. | |
| 2010/0292724 A1 | 11/2010 | Ravikumar et al. | |
| 2011/0046449 A1 | 2/2011 | Minnelli et al. | |
| 2011/0160538 A1 | 6/2011 | Ravikumar et al. | |
| 2011/0196205 A1 | 8/2011 | Hathaway et al. | |
| 2012/0080483 A1 | 4/2012 | Riestenberg et al. | |
| 2012/0277576 A1 | 11/2012 | Lui | |
| 2014/0276666 A1 | 9/2014 | Malkowski | |
| 2017/0156789 A1 | 6/2017 | Ravikumar et al. | |
| 2017/0224413 A1 | 8/2017 | Ravikumar et al. | |

FOREIGN PATENT DOCUMENTS

| | | |
|---|---|---|
| CN | 102510739 A | 6/2012 |
| EP | 0647429 A2 | 4/1995 |
| EP | 1516592 A2 | 3/2005 |
| JP | S58133348 U | 9/1983 |
| JP | H0215159 A | 1/1990 |
| JP | H09512732 A | 12/1997 |
| JP | 2003510137 A | 3/2003 |
| JP | 2008253585 A | 10/2008 |
| JP | 2009529983 A | 8/2009 |
| JP | 2010207260 A | 9/2010 |
| JP | 2011212458 A | 10/2011 |
| JP | 2012165958 A | 9/2012 |
| JP | 2013106771 A | 6/2013 |
| JP | 2013248222 A | 12/2013 |
| WO | 9714457 A1 | 4/1997 |
| WO | 2007050969 A2 | 5/2007 |
| WO | 2012044815 A1 | 4/2015 |

* cited by examiner

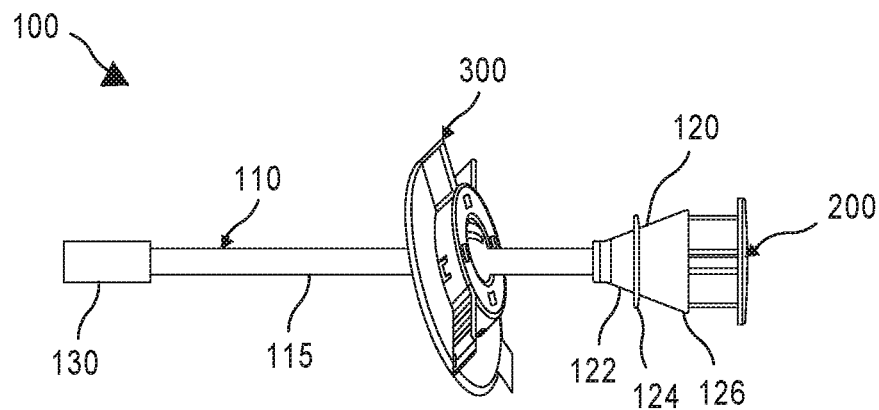
Fig. 1
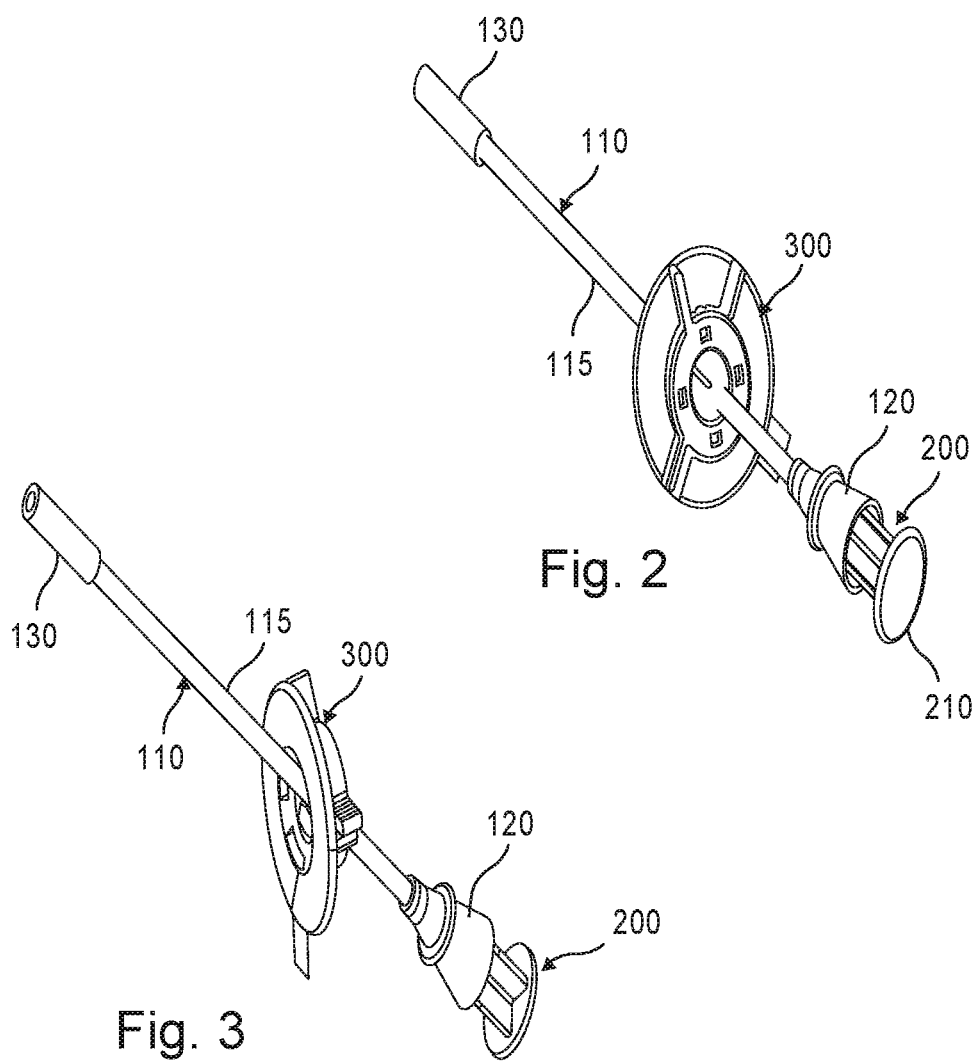
Fig. 2
Fig. 3

EXCHANGER SURGICAL ACCESS PORT AND METHODS OF USE

CROSS-REFERENCE TO RELATED APPLICATION

The present application is a Continuation of U.S. patent application Ser. No. 14/798,987, filed Jul. 14, 2015, which claims the priority benefit of U.S. Provisional Patent Application No. 62/024,999, filed Jul. 15, 2014, the entire disclosures of which are incorporated by reference in their entirety.

TECHNICAL FIELD

The present disclosure relates to surgical instruments and methods of their use, and more particularly to minimally invasive surgical instruments, an exchanger surgical access port, and methods of using an exchanger surgical access port so that multiple instruments can be used therein.

Examples of minimally invasive surgical assemblies and related equipment are described in U.S. Pat. No. 7,766,937 to Ravikumar, U.S. Pat. No. 8,230,863 to Ravikumar et al., U.S. Pat. No. 8,313,507 to Ravikumar, U.S. Pat. No. 8,133,255 to Ravikumar et al., U.S. patent application Ser. No. 11/685,522 to Ravikumar et al. (published as U.S. Patent Pub. No. 2007/0250112), U.S. patent application Ser. No. 12/503,035 to Ravikumar (published as U.S. Patent Pub. No. 2010/0016884), U.S. patent application Ser. No. 11/610,746 to Ravikumar et al. (published as U.S. Patent Pub. No. 2007/0282170), and U.S. patent application Ser. No. 12/689,352 to Ravikumar et al. (published as U.S. Patent Pub. No. 2010/0292724), all of which are incorporated by reference herein in their entireties.

DESCRIPTION OF RELATED ART

Over the last two decades, minimally invasive surgery has become the standard for many types of surgeries which were previously accomplished through open surgery. Minimally invasive surgery generally involves introducing an optical element (e.g., laparoscopic or endoscope) through a surgical or natural port in the body, advancing one or more surgical instruments through additional ports or through the endoscope, conducting the surgery with the surgical instruments, and withdrawing the instruments and scope from the body. In laparoscopic surgery (broadly defined herein to be any surgery where a port is made via a surgical incision, including but not limited to abdominal laparoscopy, arthroscopy, spinal laparoscopy, etc.), a port for a scope is typically made using a surgical trocar assembly.

The trocar assembly often includes a port, a sharp pointed element (trocar) extending through and beyond the distal end of the port, and at least in the case of abdominal laparoscopy, a sealing valve on the proximal portion of the port. The term trocar typically includes a combination of cooperating elements such as a cannula, a seal housing, and an obturator. First the obturator cuts or pierces the body wall so that the cannula may be inserted. The cannula defines a pathway through a body wall through which the surgical instruments are inserted. Finally, the seal housing provides an isolation of the cannula so that if insufflation is employed the body region remains distended and sealed. All three components are usually fitted together and used as a single unit for passage by one or more surgical instruments through the body wall and into a body cavity.

Laparoscopic surgery typically begins as the surgeon inserts a large bore needle through a body wall and into the internal region associated with the body wall. Next, an inflation or insufflation gas is pumped into the internal region until it is properly distended. The body wall and internal region are now ready for insertion of trocars.

Typically, a small incision is made in the skin at a desired location in the patient. The incision may be made via a scalpel or other sharp instrument. The trocar assembly, with the trocar extending out of the port, is then forced through the incision via the obturator which cuts or pierces the body wall, thereby widening the incision and permitting the port to extend through the incision, past any fascia, and into the body (cavity). The trocar is then withdrawn, leaving the port in place.

If not already distended, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include diameters of about 5 mm, 10 mm, and 12 mm, which are sized to permit variously sized laparoscopic instruments to be introduced therethrough including, e.g., graspers, dissectors, staplers, scissors, suction/irrigators, clamps, forceps, biopsy forceps, etc. While 5 mm diameter trocar ports are relatively small, in some circumstances where internal working space is limited (e.g., children), it is difficult to place multiple 5 mm diameter ports in the limited area of the patient. In addition, 5 mm diameter trocar ports tend to limit movement of instruments inside the abdominal cavity to a great extent. Such a conventional 5 mm diameter trocar has a sealing valve and sealing mechanism and therefore the opening for the surgical instrument is limited.

Further, while laparoscopic surgery has reduced the trauma associated with various surgical procedures and has concomitantly reduced recovery time from these surgeries, there always remains a desire in the art to further reduce the trauma to the patient.

One area of trauma associated with laparoscopic surgery identified by the inventors hereof as being susceptible of reduction are the scars which result from the trocar ports used. In many laparoscopic surgeries, three or more trocar incisions are made. For example, in laparoscopic hernia repair surgery, four trocar incisions are typically made, with one incision for insufflating the abdomen and inserting the optical device, two incisions for trocar ports for inserting graspers therethrough, and a fourth port for passing a stapler therethrough. Those skilled in the art and those who have undergone surgical procedures understand that even the 5 mm diameter trocar ports leave holes which must be stitched and which result in scars. Scar tissue may affect the internal portion of the fascia as well as the cosmetic appearance of the skin, which may be detrimental for the patient or even a surgeon if that area of the skin is subject to a later incision or medical procedure.

A second area of trauma associated with laparoscopic surgery relates to trauma resulting from the manipulation (e.g., angling) of the trocar ports required in order to conduct the surgery due to inexact placement. Angling of the port can cause tearing at the incision periphery. Such tearing can lead to extensive scar tissue and in general an extension of the incision area. Again, conventional 5 mm diameter trocars including a valve and sealing mechanism are hard to angle in regard to the opening for the surgical instrument. Thus a need exists for a surgical access port which is not subject to tearing fascia at the point of incision into the patient.

A further problem with surgical instruments including a needle tip is inadvertent needle penetration in tissue and resulting scarring or even more serious complications during the surgery if other tissue is nicked or penetrated unintentionally. Indeed, placing a sharp instrument such as an inflation needle or trocar obturator through a body wall and into an associated internal region comes with considerable risk. The human abdomen, for example, is a tightly packed region that is filled with delicate structures and organs. There is no open space between the abdominal wall and those structures or organs until inflation gas is inserted and a pneumoperitoneum is established. Great care must be taken when placing inflation needles so as to avoid penetration of intestine, bowel or other structures. Even after insufflation is established, there is a risk of injury during placement of additional sharp instruments through the distended body wall. The body wall is comprised of skin, muscle, fat, and a thin membrane. The wall may be thick, muscular and tough or it may be lean and soft. As such, placement of a sharp obturator through the body wall requires great skill and knowledge of what lies within the internal region. The force required to insert a sharp trocar through a body wall can exceed forty pounds in some cases. This applied force easily overcomes the pneumoperitoneum and forces the body wall down and against delicate structures where there is the danger of piercing or cutting those structures.

To combat the need for such force of insertion of a typical trocar, some surgeons have also used a technique referred to as a "cut down" procedure where successive small incisions are made until the body wall is cut through, at which time a blunt trocar or a trocar obturator is inserted with a certain level of force. This process may incur less force but it is time-consuming and may leave a deeper and larger scar. As such, a need exists for a surgical access port which is easier to insert into a body wall.

A further need exists for a surgical access port which is secured to the outer fascia of the patient. Certain known securing means include pinching of the skin which can lead to scarring and other complications, while other securing means include various adhesive measures. A less obtrusive (less scarring) yet secure means is needed so that the trocar does not move when in use.

There continues to be a need in the art for a surgical access port which reduces trauma to the patient, reduces complications to the patient, does not lead to extension of the incision area, does not lead to increased scar tissue generation, is easy to make and use, and improves safety while reducing costs to health care providers and patients and reducing the surgical time for a procedure which in turn may reduce costs and complications. The inventive surgical access port includes a trocar having a cannula with a diameter of about 1 mm to about 3 mm including a removable obturator having a diameter of about 1 mm to about 3 mm which is capable of insertion into a patient's skin and body wall.

While conventional trocars including an obturator are known, the conventional art includes a cannula with a diameter exceeding about 5 mm. Thus there exists a need for a surgical access port which includes a smaller diameter cannula.

Further, the conventional trocars are inserted manually through force and thus a need exists where a surgical access port may be inserted via a surgical instrument itself having a needle for insertion into the patient's skin and body wall. These and other needs are met by the inventive surgical access port and method for insertion and method of use.

Further, conventional trocars include a valve and sealing means so as to prevent gas leakage during insufflation. A need exists for a more streamlined trocar without an additional valve or sealing means while still maintaining sufficient insufflation during surgery. A need exists for a surgical access port without a valve or sealing means while still maintaining an acceptable gas pressure level or minimal leakage.

Other advantages of the present invention will become apparent from the following description and appended claims.

SUMMARY

According to one aspect, the disclosure describes an access port assembly. The access port assembly comprises an obturator having a longitudinally extending obturator shaft including a sharp tip disposed at a distal end of the obturator shaft and a handle disposed at a proximal end of the obturator shaft, the handle including at least one finger extending spaced from the handle. The access port assembly further comprises a surgical access port having a cannula defining a hollow cannula shaft, and a tapered hub attached to a proximal end of the cannula. The tapered hub includes at least one inner ring configured to abut against the at least one finger while the obturator is inserted within the cannula of the surgical access port.

According to one aspect, the disclosure describes a surgical instrument access port assembly. The surgical instrument access port assembly comprises a surgical instrument having a needle lumen extending in a longitudinal direction including a needle tip at a distal end, and a body portion at a proximal end, the body portion including at least one recess or finger. The surgical instrument access port assembly further comprises a surgical access port having a cannula defining a hollow cannula shaft, and a tapered hub attached to a proximal end of the cannula. The tapered hub includes at least one inner ring configured to abut against the at least one recess or finger while the surgical instrument is inserted into the cannula of the surgical access port.

According to one aspect, the disclosure describes a method of using a surgical instrument access port assembly comprising a surgical instrument having a needle lumen extending in a longitudinal direction including a needle tip at a distal end, and a body portion at a proximal end, the body portion including at least one recess or finger, and including a surgical access port having a cannula defining a hollow cannula shaft, and a tapered hub attached to a proximal end of the cannula, the tapered hub including at least one inner ring configured to abut against the at least one recess or finger while the surgical instrument is inserted into the cannula of the surgical access port. The method comprises piercing a hole in a body wall with the needle tip of the needle lumen, inserting at least a portion of the needle lumen through the hole into a body cavity, advancing the surgical access port along the needle lumen in a distal direction towards the hole, and inserting the cannula of the surgical access port through the hole into the body cavity.

BRIEF DESCRIPTION OF THE DRAWINGS

FIG. 1 shows a side view of an exemplary surgical access port assembly in accordance with aspects of the disclosure.

FIG. 2 shows a first perspective view of the exemplary surgical access port assembly of FIG. 1 in accordance with aspects of the disclosure.

FIG. 3 shows a second perspective view of the exemplary surgical access port assembly of FIG. 1 in accordance with aspects of the disclosure.

DETAILED DESCRIPTION

Figure 4:
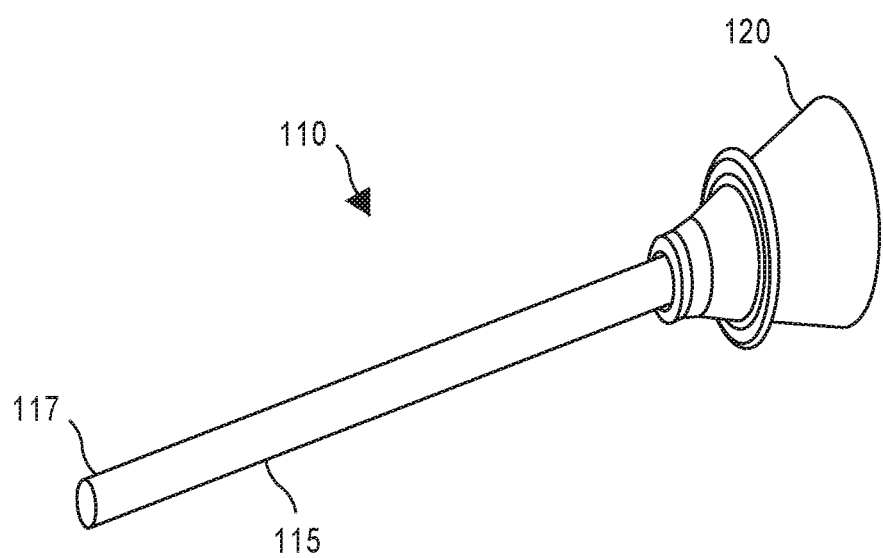
FIG. 4 shows a side perspective view of an exemplary surgical access port in accordance with aspects of the disclosure.

In accordance with aspects of the disclosure, a surgical access port assembly 100 may include a surgical access port with a cannula, a hub, and an obturator. In one aspect, the surgical access port may be connected or usable with a laparoscopic instrument having an elongated cannula such that the surgical access port is placed over the cannula of the laparoscopic instrument and thus does not require an obturator as the laparoscopic surgical instrument. In one aspect, the laparoscopic instrument may include a needle and the needle may pierce a patient's skin and thereafter the surgical access port may be inserted into the surgical site.

Now referring to the drawings, wherein like reference numerals refer to like elements, FIG. 1 shows the surgical access port assembly 100, which may include a surgical access tube or a cannula 115 having a diameter of about 1 mm to about 5 mm thereby reducing trauma to the patient and eliminates the need for a larger incision point or for a series of small incision cuts through the various layers of fascia. In one aspect, the diameter of the cannula 115 may be less than about 3 mm, such as between 2.3 mm to about 2.96 mm. The incision point may be 5 mm or less depending on a diameter of the distal tip portion of the obturator or the needle of the laparoscopic surgical instrument.

Referring now to FIGS. 1-3, the surgical access port assembly 100 may include a surgical access port 110, an obturator 200, and a locking mechanism 300. In one aspect, the obturator 200 may be eliminated and the surgical access port assembly 100 may be affixed over a cannula of a surgical instrument as will be described in further detail below with reference to FIGS. 16-25.

As shown in FIGS. 1-6, the surgical access port 110 may have an elongated cannula 115. A distal end 117 of the elongated cannula 115 may be blunt or beveled. The elongated cannula 115 may define a hollow cannula shaft 116, through which surgical instruments or the obturator 200 may be inserted and pass through when the surgical access port 110 is in use. The elongated cannula 115 may include a proximal end connected to a hub 120. The hub 120 may define an outer diameter which expands outwardly, relative to a central axis, in a proximal direction from the proximal end of the elongated cannula 115. The hub 120 may include a portion 122 connected to the proximal end of the elongated cannula 115, an outer ring portion 124 which may be used by a surgeon for manual manipulation of the surgical access port 110, and a tapered open end portion 126 of the hub 120 with a diameter exceeding that of the elongated cannula 115. The tapered open end portion 126 of the hub 120 may be capable of housing the obturator 200, as well as providing access for surgical instruments and devices during surgery. The surgical access port 110 may be made of various materials that may have rigid material properties and may include metals or plastics. For example, the materials may include stainless steel, liquid crystal polymer or polycarbonate, glass-filled polycarbonate, or the like. The material should be compatible with the human fascia, body wall and any body cavity into which the surgical access port 110 is inserted so as to prevent or reduce any allergic reaction by the patient upon insertion. Of course, other compatible materials are of course contemplated.

Additionally, the surgical access port 110 may be covered or coated on the outside, and/or within the hollow cannula shaft 116, with an insulating material (not shown) to prevent electrical current transfer to the patient, for instance, upon inadvertent contact with an electrical surgical apparatus such as a monopolar or bipolar surgical instrument. The insulating material may be a plastic shrink wrap or any other insulating materials such as plastics, polymers, elastomers and the like, and combinations thereof.

Figure 5:
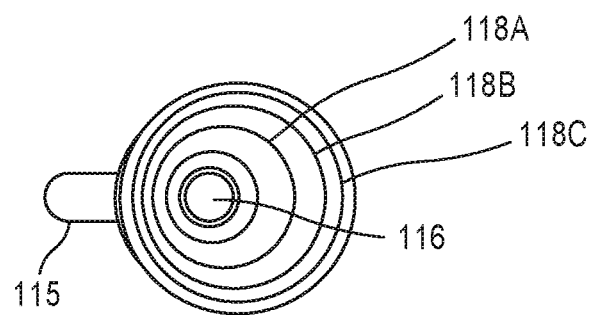
FIG. 5 shows a top perspective view of the exemplary surgical access port of FIG. 4 in accordance with aspects of the disclosure.
Figure 6:
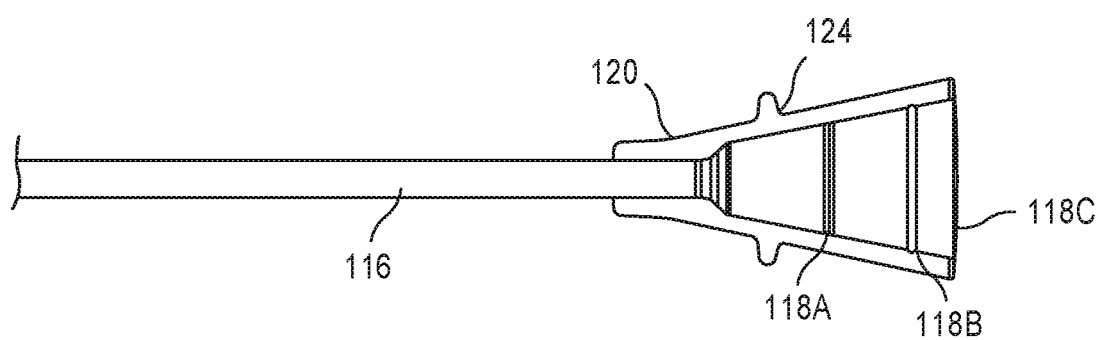
FIG. 6 shows a cross-sectional side view of the exemplary surgical access port of FIG. 4 in accordance with aspects of the disclosure.

Turning to FIGS. 4-6, the hub 120 of the surgical access port 110 may have an inner portion including at least one inner ring, shown in FIGS. 5 and 6 as inner rings 118A, 118B and 118C. Each of the inner rings 118A, 118B, 118C, may define a rib or groove on an inner surface of the hub 120. The inner rings 118A, 118B, 118C may be used as a securing means for attaching and securing the obturator 200 via fingers 230 to the hub 120. In one aspect, the inner rings 118A, 118B, 118C may be used to connect the surgical access port 110 to a surgical instrument or device over such instrument's cannula. In one aspect, at least one of the inner rings 118A, 118B, 118C may include an O-ring made with a compressible material so as to seal a portion of the surgical access port 110 and deter leakage of gas during surgical insufflation. For example, the O-ring may be made of rubbers, foams, plastics, silicones, fluorocarbons, polymers, elastomers, nitriles and the like, including combinations thereof. In one aspect, the at least one inner ring 118A, 118B, 118C including the O-ring may abut the fingers 230 of the obturator 200 when the obturator 200 is secured to the surgical access port 110. Alternatively, the at least one inner ring 118A, 118B, 118C including the O-ring may located downstream or upstream of the fingers 230 of the obturator 200 when the obturator 200 is secured to the surgical access port 110.

Figure 7:
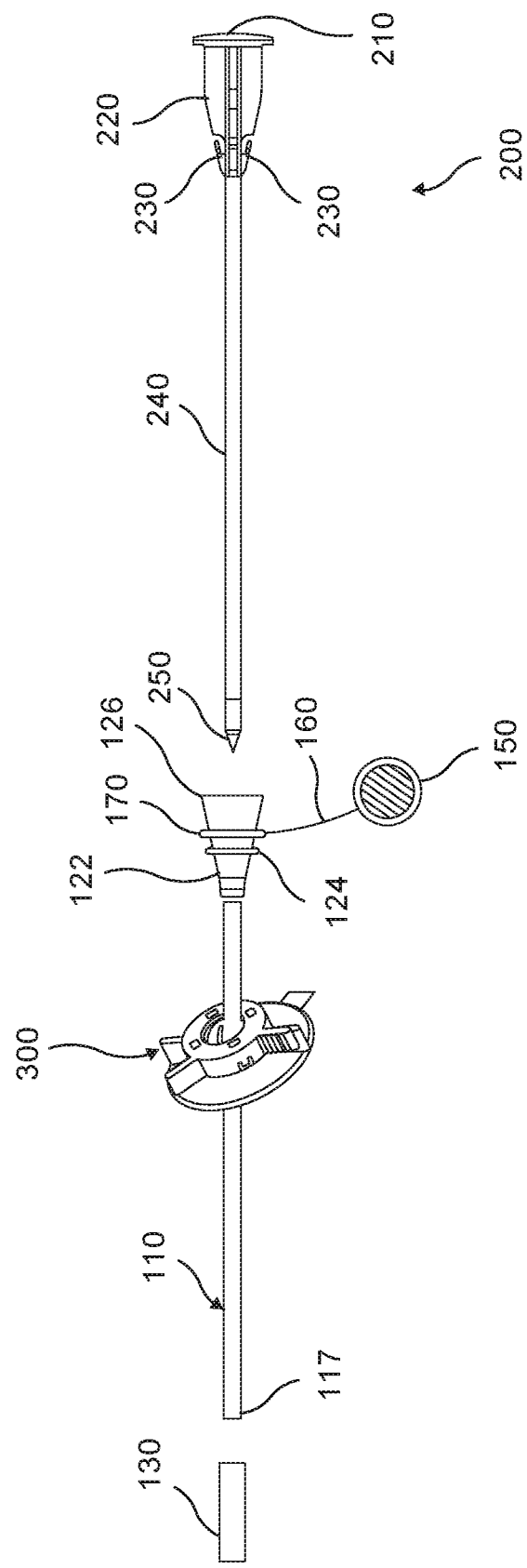
FIG. 7 shows an exploded view of an exemplary surgical access port assembly in accordance with aspects of the disclosure.

The surgical access port 110 may include a cap 150 (as shown in FIG. 7) connected to the hub 120 via a cap tether 160 and a ring 170 secured to the hub 120. In one aspect, once the surgical access port 110 has been inserted into the patient's body during surgery, there may be instances where a surgical instrument is not employed through the surgical access port 110. The cap 150 may be mounted or attached to the tapered open end portion 126 of the hub 120 in order to seal the surgical access port 110, thereby preventing gas leakage associated with surgical insufflation and/or to prevent contaminates from entering the body cavity.

For instance, when one surgical instrument is removed from the surgical access port 110 and before another surgical instrument can be inserted into the surgical access port 110, the cap 150 may be secured to the tapered open end portion 126. As a further safety measure, the cap 150 may also be mounted or attached to the tapered open end portion 126 of the hub 120, prior to the surgical access port 110 being used on a patient, to prevent contaminates from entering into the hollow cannula shaft 116. In one aspect, a tip 130 may be employed to engage the distal end 117 of the surgical access port 110 to also prevent contaminates from entering into the hollow cannula shaft 116. Additionally, the tip 130 may also be used as a cover for a sharp tip 250 of the obturator 200 when the obturator 200 is not in use, thereby serving as a guard for the sharp tip 250 and preventing accidental needle tip trauma.

Figure 8:
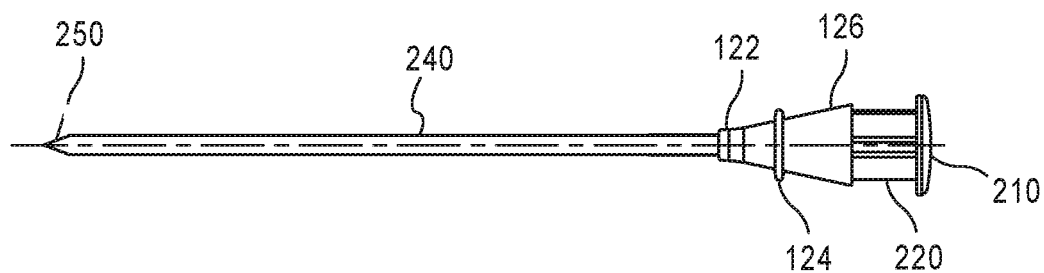
FIG. 8 shows a side view of an exemplary obturator in accordance with aspects of the disclosure.
Figure 9:
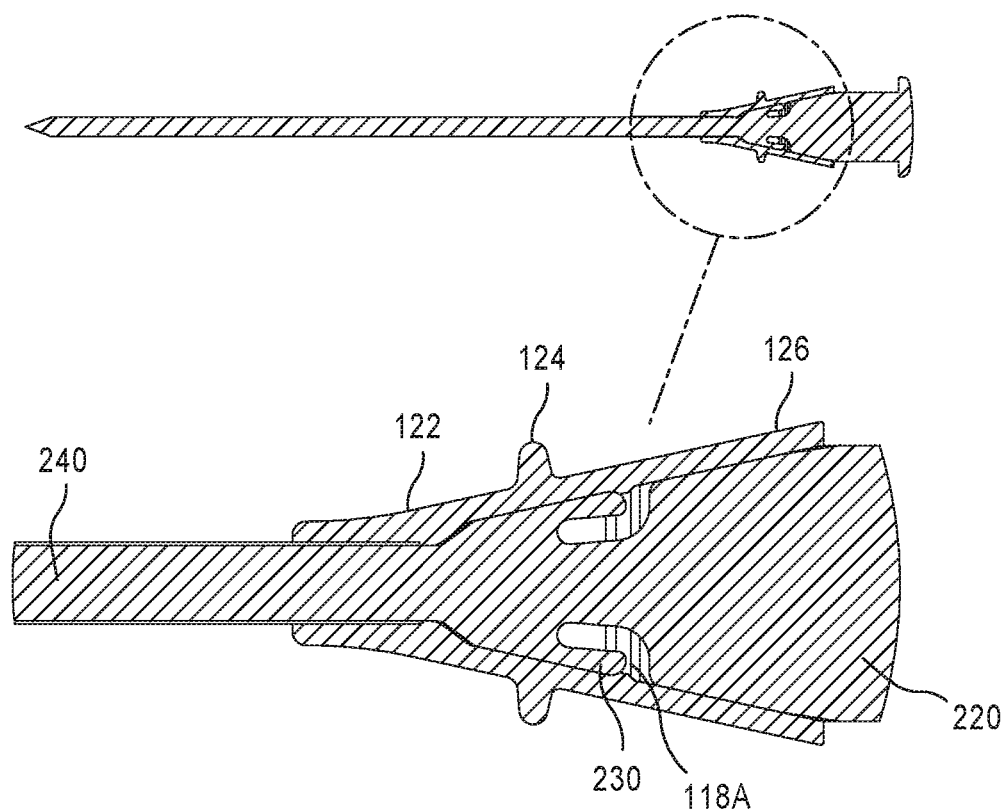
FIG. 9 shows a cross-sectional side view of an exemplary obturator in accordance with aspects of the disclosure.

Turning to FIG. 7, the obturator 200 may include an obturator shaft 240, which may include a diameter that is less than or equal to a diameter of the hollow cannula shaft 116. The diameter of the obturator shaft 240 may be less than about 3 mm, and may be in one aspect, between 2.3 mm to about 2.96 mm. As shown in FIGS. 7-9, the sharp tip 250 may be provided at the distal end 117 of the obturator shaft 240. The sharp tip 250 may be conical in shape, blunt in shape, or may include a needle or blade (not shown) to assist in insertion of the surgical access port 110 into a patient's fascia and through the body cavity wall. A handle 220 may be disposed at a proximal end of the obturator shaft 240, and may be used by a user for manual manipulation of the surgical access port assembly 100. The handle 220 may include an end or handle 210 for grasping by the user, and at least one finger 230 for securing the obturator 200 to at least one inner ring 118A, 118B, 118C of the hub 120, or an inner surface of the hollow cannula shaft 116

As shown in FIGS. 8 and 9, the finger 230 may connect to an inner ring 118A by flexing and snapping into place, but may be moved by light manipulation of the handle 210 by the user so as to remove the obturator 200 once the surgical access port 110 is in place on the patient. In use, the obturator 200 may be directed to penetrate the patient's fascia and a body wall to provide the surgical access port 110 and its cannula 115 with access across the body wall and into a body cavity. The obturator 200 may be made of various materials which are compatible with the human fascia, body wall and any body cavity into which it is inserted so as to prevent or reduce any allergic reaction by the patient upon insertion. The obturator 200 may be made may be a rigid plastic, rubber, polymer, elastomer, metal, and the like, and combinations thereof. Of course, other compatible materials are of course contemplated.

The surgical access port assembly 100 may further include a locking mechanism 300 to secure the surgical access port 110 to an outer layer of fascia of the patient.

Figure 10:
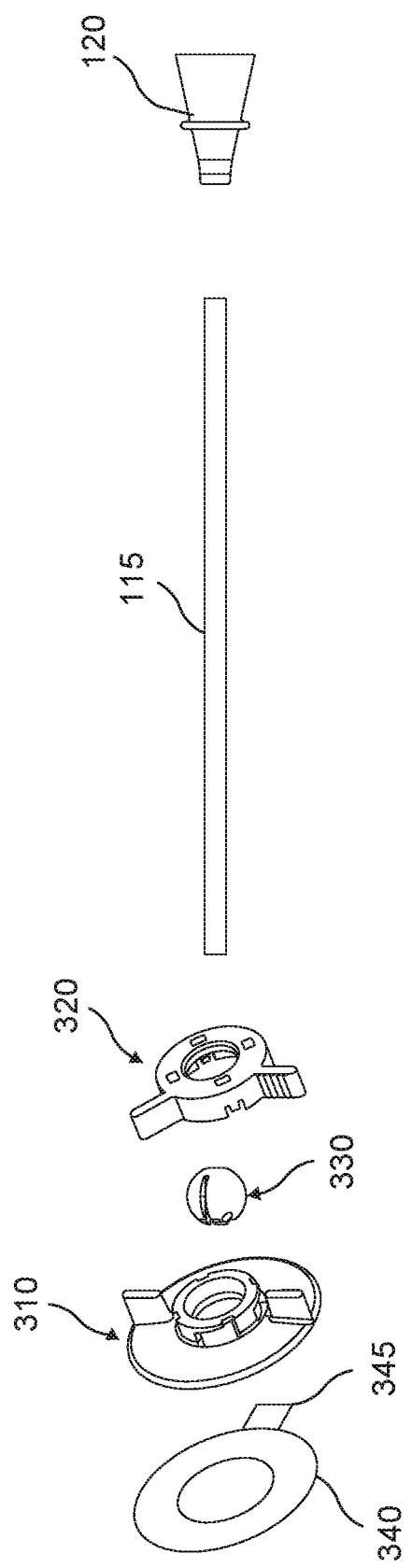
FIG. 10 shows an exploded view of an exemplary surgical access port assembly in accordance with aspects of the disclosure.
Figure 11:
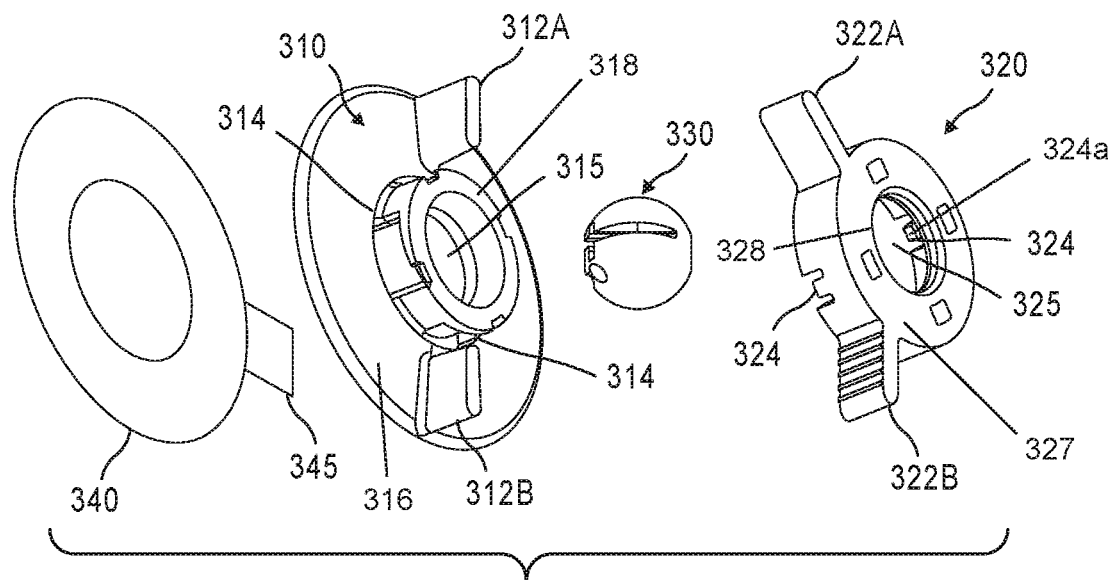
FIG. 11 shows an exploded view of an exemplary locking mechanism assembly in accordance with aspects of the disclosure.

FIGS. 10 and 11 illustrate exploded views of the locking mechanism 300. The locking mechanism 300 may include a lock base 310 having an aperture 315 through which the cannula 115 of the surgical access port 110 may be inserted through. The lock base 310 may include at least one tab 312A, 312B, and preferably two tabs spaced apart from one another to provide a grip to the user and/or provide limits to a locking member 320. The lock base 310, including the tabs 312A, 312B, form a part of the locking mechanism 300 that is secured to the outer fascia layer of the patent such that the surgical access port 110 remains in a set position relative to the patient when in use. The lock base 310 may further include at least one screw thread or ramp 314 which connectable with at least one snap or finger 324 of the locking member 320.

The locking member 320 may define an aperture 325 through which the cannula 115 of the surgical access port 110 is inserted. The locking member 320 may include at least two lock tabs 322A, 322B which may extend radially from the locking member 320 and may be used as a grip by the user, and/or to limit the rotational movement of the locking member 320 relative to lock base 310. The locking mechanism 300 may be made of various materials which are compatible with the human fascia so as to prevent or reduce any allergic reaction by the patient upon adhesion thereof. The locking mechanism 300 may be made may be a rigid plastic, rubber, polymer, elastomer, metal, and the like, and combinations thereof. Of course, other compatible materials are of course contemplated.

The locking member 320 of the locking mechanism 300 may be rotatably attached to the lock base 310. In one aspect, the locking mechanism 300 may include a plurality of snaps or fingers 324, which may correspond to a number of screw threads 314 of the lock base 310. Each of the plurality of snaps may extend downwardly parallel to a central axis of the locking member 320. Each of the snaps or fingers 324 may further include a radially extending protrusion to engage with a groove of a respective screw thread or ramp 314. The snaps or fingers 324 may engage with the screw threads or ramps 314, and the locking member 320 may be rotated relative to the lock base 310. In one aspect, as the locking member 320 is rotated clockwise to a locked position, the snaps or fingers 324 may be guided by the grooves of the screw threads to displace the locking member 320 axially towards the lock base 310. Conversely, as the locking member 320 is rotated counter-clockwise to an unlocked position. The snaps or fingers 324 may be guided by the grooves of the screw threads to displace the locking member 320 axially away the lock base 310. Additionally, the groove of the screw threads 314 may cooperate with a taper of the aperture 315 such that as the locking member 320 is threaded axially towards the lock base 310, the snaps or fingers 324 may apply a compressive force inwardly towards a center of the aperture 315, and may cause the aperture 315 is compress inwardly. Of course, it will be appreciated to one skilled in the art in view of this disclosure that the direction of the threading may be reversed such that a counter-clockwise rotation of the locking member 320 may be used to place the locking mechanism 300 in the locked position, while a clockwise rotation of the locking member 320 may be used to place the locking mechanism 300 in the unlocked position.

Figure 12:
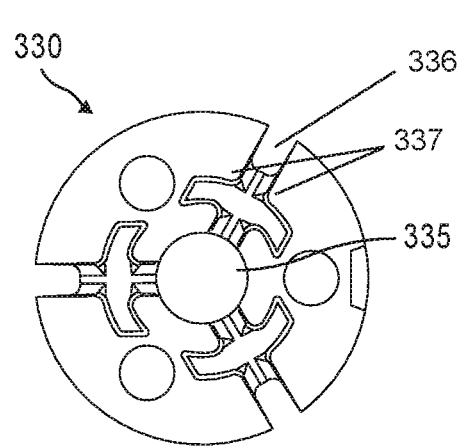
FIG. 12 shows a bottom view of an exemplary ball of the locking mechanism of FIG. 11 in accordance with aspects of the disclosure.
Figure 13:
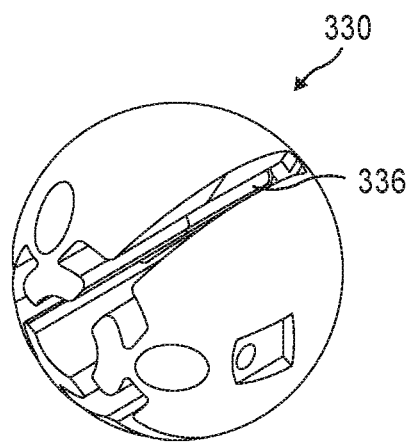
FIG. 13 shows a perspective view of the exemplary ball of the locking mechanism of FIG. 11 in accordance with aspects of the disclosure.

The locking mechanism 300 may further include a ball 330, shown in detail in FIGS. 12 and 13, and may be disposed between the lock base 310 and the locking member 320. The ball 330 may be housed between the apertures 315 and 325 of the lock base 310 and the locking member 320, respectively. The ball 330 may include an opening or aperture 335 through which the cannula 115 of the surgical access port 110 may be inserted. The ball 330 may be made of a material which is compressible, such as plastic, polymers, elastomers, rubber or the like. The ball 330 may also include at least one slit 336 which is compressible when the locking mechanism 300 is in a locked position, as will be described in further detail below. The slit 336 may enable the surgical access port 110 to be moved at an angle within the apertures 315, 325, and 335. In one aspect, when the locking mechanism 300 is in an unlocked position, the ball 330 may be rotated about 45° relative to a horizontal plane defined by the lock base 310 and 45° relative to a horizontal plane of the locking member 320. The locking mechanism 300 may then be placed in a locked position, whereby the locking member 320 compresses the aperture 315 inwardly, which may in turn cause the ball 330 to compress inwardly by displacing at least a surface of the ball 330 via the at least one slit 336, thus securing a position of the ball 330 relative to the lock base 310 and the locking member 320.

Once an angle of the surgical access port 110 is chosen or finalized, the locking mechanism 300 is actuated by rotating the lock tabs 322A, 322B relative to the base tabs 312A, 312B. In one aspect, the user may squeeze or pinch tabs 312A and 322A together using a thumb and index finger, for example, which may in turn squeeze and collapse the at least one slit 336 of the ball 330. To unlock the locking mechanism 300 the user may squeeze or pinch the opposite tabs, such as tabs 312B and 322B together, using a thumb and index finger, which may in turn release the at least one slit 336 of the ball 330.

The locking mechanism 300 may further be secured to the patient's skin and thus secure the surgical access port 110 when it is inserted into the patient's fascia. An underside of the base 310 may be coated with an adhesive and the adhesive may be covered and protected by a paper liner 340 prior to use. The paper liner 340 may include a tab 345 to assist the user in gripping and removing the paper liner 340 from the base 310. In one aspect, the paper liner 340 may be perforated or may include a separation line to assist in the removal of the paper liner 340 even if one or more of the surgical access port 110, the obturator 200, and the surgical instrument has been inserted through the locking mechanism 300. Once the paper liner 340 is removed, the adhesive is exposed such that the adhesive may be placed onto the fascia of the patient to thereby secure the locking mechanism 300 and surgical access port 110 to the patient's fascia. Any known adhesive compatible to the fascia of a patient may be used. By securing the locking mechanism 300 to the fascia of the patient, the surgical access port 110 may be secured without the need for pinching or other securing means which may be harmful to the patient. This benefit is of immediate notice and effect to the surgeon and to the patient's fascia.

As shown in FIGS. 10 and 11, the lock base 310 may comprise of a base platform 316, having a flat bottom surface, on which an adhesive layer and a peelable protective paper liner 340 may be applied, a top surface which defines at least two finger tabs 312A, 213B, and a central ring 318 with an inner surface defining the aperture 315. The central ring 318 may include a slightly tapered frustoconical inner surface for receiving the ball 330 and may further include at least two or three separate outer screw threads or ramps on an outer surface which are recessed into the central ring 318 and start at the top surface of the ring 318 and descend as they extend clockwise about the ring 318 until they reach a top of the base platform 316, thereby forming small ledges for purposes explained hereinafter.

In one aspect, the ball 330 may be a hollow plastic ball provided with opposite circular openings sized to closely receive the cannula 115 of the surgical access port assembly 100, and a plurality of slits 336 which extend about 120° from the opening in the direction of the axis defined by openings. With the slits 336, the ball 330 may be compressed such that if a circumferential force is applied to the ball 330, the lobes 337 formed between the slits 336 will move toward each other. The locking member 320 may comprise a cap with at least two extending arms or tabs 322A, 322B. The cap 326 may have a top wall 327 with a central opening 328 defining the aperture 325 through which the top portion of the ball 330 can extend. The cap 326 may also have a side wall with cut-outs which define engagement fingers or snaps or fingers 324. The engagement fingers 324 may have bosses which are sized to ride in the ramps of the central ring 318 of the lock base 310 and the inward facing bosses may be ramped or beveled.

With reference to FIGS. 10 and 11, assembly of the locking mechanism 300 will now be described. In one aspect, the ball 330 may be placed between the lock base 310 and the locking member 320 with the bosses 324a of the engagement fingers 324 being forced over the ledges and into engagement with the ramps 314 of the lock base 310. In this position a bottom of the side wall of the cap 326 of the locking member 320 is spaced relative to a top surface of the base platform 316 of the lock base 310, and the ball 330 is free to rotate as guided by the ring 318 and central opening 325. Thus, when the cannula 115 of the surgical access port assembly 100 is inserted through the circular openings 335 of the ball 330, the cannula 115 will have considerable freedom of movement, limited only by the size of the central opening 325 of the locking member 320 and the frustoconical central opening 315 of the lock base 310. In one aspect, the locking mechanism 300 may be provided a freedom of movement of at least 45° relative to the vertical in all directions for the cannula 115 of the present disclosure, thereby resulting in a range of angles for insertion of the surgical access port assembly 100. However, when the locking member 320 is rotated clockwise relative to the lock base 310 (typically by squeezing finger tabs 312A, 322A together with a thumb and forefinger), the bosses 324a ride down the ramps 314 and pull the locking member 320 closer to the lock base 310. Since the ball 330 cannot move downward in the ring 318, the central opening 315 provides a circumferential force to the ball 330 (i.e., it compresses the ball), thereby forcing the lobes 337 inward, and applying friction to the cannula 115 of the surgical access port assembly 100, when installed. As a result, not only is the cannula 115 locked in place relative to the ball 330, but the ball 330 is fixed in its rotational orientation relative to the locking mechanism 300. The ball 330 and cannula 115 may be released by rotating the locking member 320 counterclockwise relative to the lock base 310 (typically by squeezing the other finger tabs 312B, 322B together). The locking member 320, however, cannot lift off the lock base 310 because the ledges act as stops.

Figure 14:
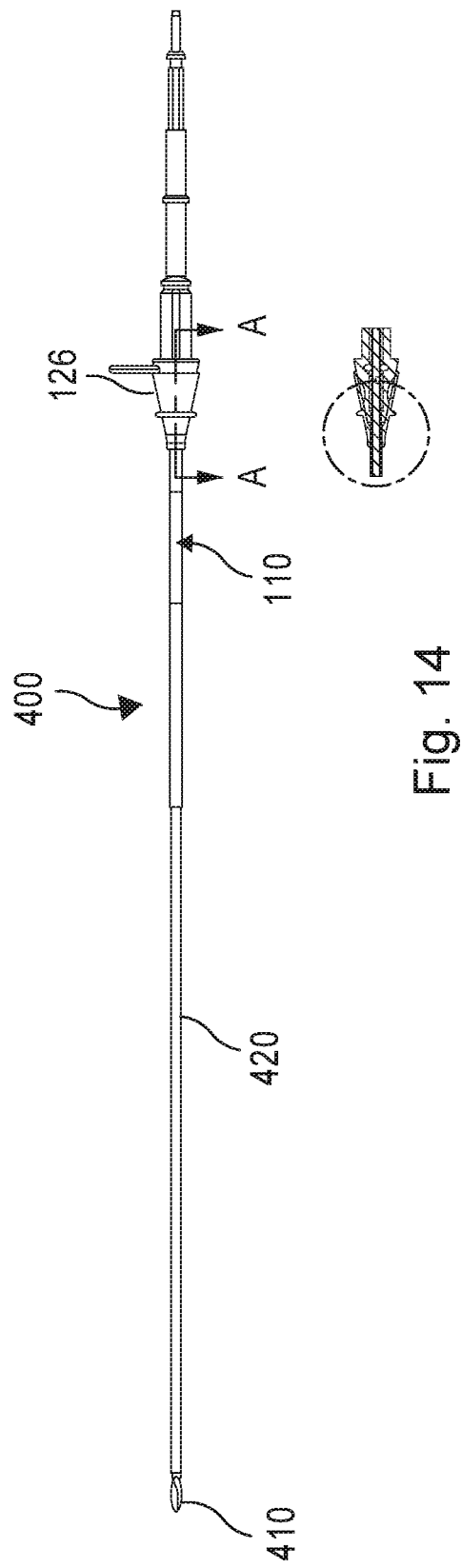
FIG. 14 shows a side view of an exemplary surgical access port including a needle lumen in accordance with aspects of the disclosure.
Figure 15:
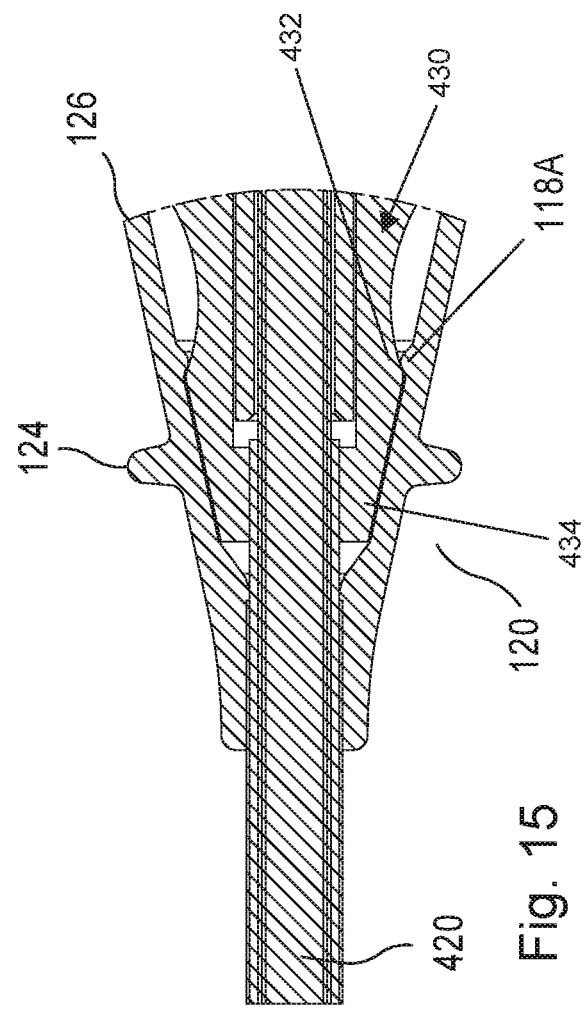
FIG. 15 shows a partial cross-sectional view of the exemplary surgical access port of FIG. 14 in accordance with aspects of the disclosure.
Figure 16:
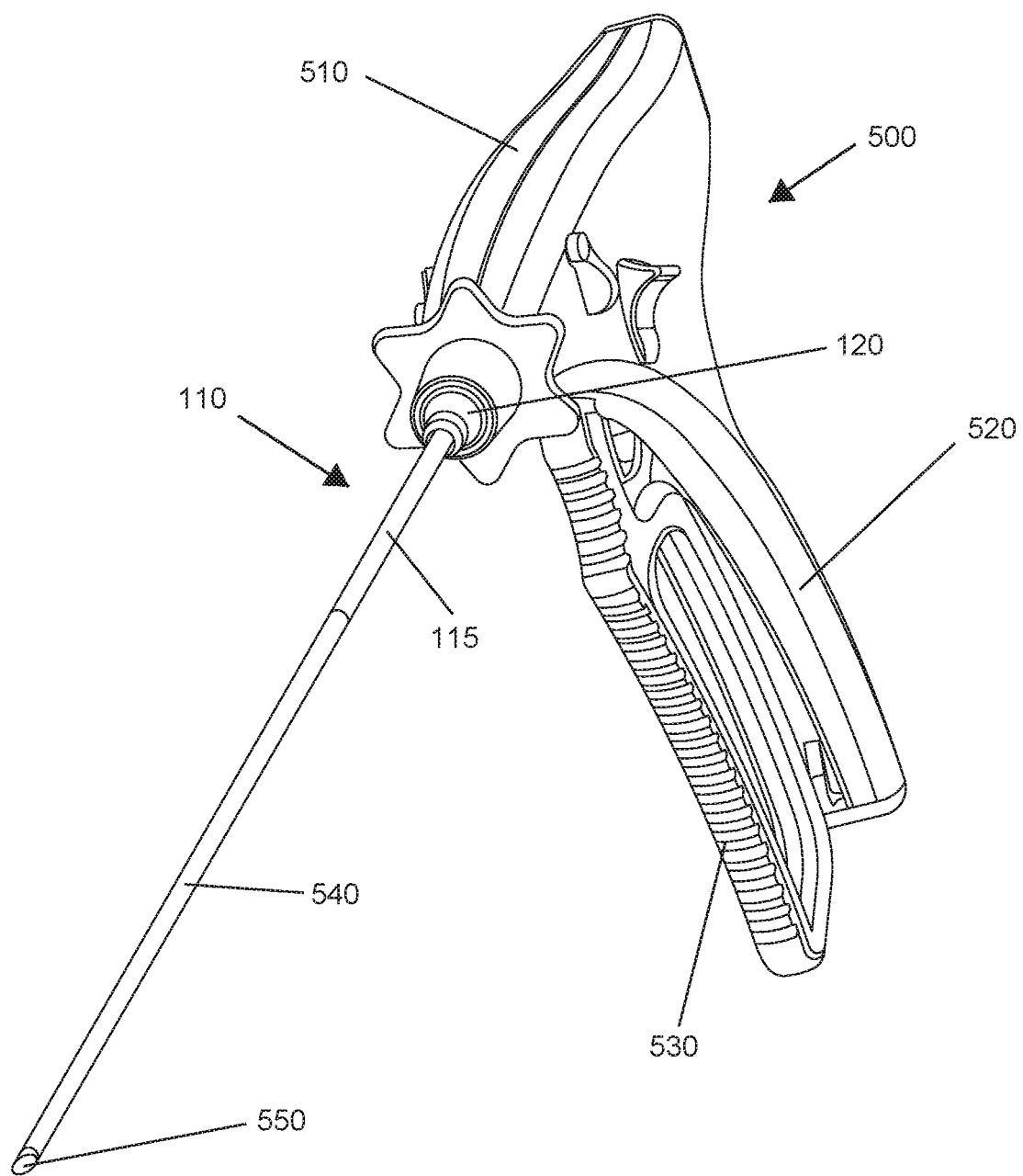
FIGS. 16-24 show methods of using an exemplary surgical access port in accordance with aspects of the disclosure.

FIGS. 14 and 15 show the surgical access port 110 connected to a needle lumen 400 having a lumen shaft 420 and an end effector such as a needle 410, in accordance with an aspect of the present disclosure. The needle lumen 400 may be inserted into a reposable handgrip surgical instrument or any other surgical instrument. The needle lumen 400 may be inserted into an aperture of the surgical access port 110 via the open end tapered portion 126 of the hub 120 and through the hollow cannula shaft 116 of the elongated cannula 115 (as shown in FIG. 6). The surgical access port 110, including the locking mechanism 300 (as generally shown in FIG. 11), may thus be connected to the needle lumen 400 by friction and light compression of the inner rings 118A, 118B, and 118C of the hub 120. In one aspect, the needle lumen 400 may comprise a body portion 430 defining a recessed portion 432. The body portion 430 may be inserted into the tapered open end portion 126 such that the recessed portion 432 extends beyond at least one of the inner rings 118A, and abuts against the inner ring 118A. In one aspect, a distal portion 434 of the body portion 430 may define a tapered outer surface corresponding with a tapered inner surface of the hub 120, as shown in FIG. 15.

The recessed portion 430 of the needle lumen 400 may be provided to abut at least one of the inner rings 118A, 118B, and 118C to thereby secure the needle lumen 400 to the hub 120. Additionally, or alternatively, fingers like the ones found on the obturator 200 may be provided to interact with one or more of the inner rings 118A, 118B, and 118C of the hub 120. In use the needle 410 of the needle lumen 400 may be used to penetrate the patient's fascia, the surgical access port 110 may be moved in an axial movement down the needle lumen 400 via manual manipulation of the outer ring 124 and the surgical access port 110 may be inserted into the patient's fascia and through the body wall.

In accordance with an aspect of the present disclosure, the surgical access port 110 including the locking mechanism 300 may be connected to a lumen of a surgical instrument or device wherein the lumen has a needle or other insertion means. The lumen of the surgical instrument may be inserted into the patient's fascia and the surgical access port 110 may be slid down the length of the lumen and inserted into the patient's fascia and the body wall. Generally, prior to the lumen of the surgical instrument being inserted into the patient, the surgical access port 110 may be attached to the lumen of a percutaneous instrument, or single needle lumen, by sliding the surgical access port 110 along a length of the lumen and connected to the instrument via the one or more inner rings 118A, 118B, 118C of the surgical access port 110. After the surgical instrument has been inserted into the patient, the surgical access port 110 may then be advanced along the lumen, away from the percutaneous instrument if in such embodiment, into the patient's fascia, through the body wall and into a body cavity. The lumen of the surgical instrument may then be removed while the surgical access port 110 remains in the body cavity. In one aspect, the removed surgical instrument may be replaced with a different surgical instrument.

In one aspect, the surgical instrument may be a needlescopic instrument having a lumen with a diameter of less than about 3 mm. In one aspect, the diameter of the lumen is between 2.3 mm to 2.96 mm, with the lumen including a needle and may include additional end-effectors such as jaws. The surgical access port 110 may be placed around the lumen of the surgical instrument while the surgical instrument is outside of the patient, but can be unsnapped from the surgical instrument, and inserted into the patient's fascia, providing a guide for additional percutaneous instruments to be inserted therein.

As shown in FIGS. 16 through 24, exemplary methods of using the surgical access port 110 together with a surgical instrument 500 will now be described. The surgical instrument 500 may include an instrument body 510, a handle 520, a trigger 530, a lumen 540, and a needle tip 550 located at a distal end of the surgical instrument 500. In one aspect, the surgical instrument 500 may be a percutaneous surgical instrument that is pre-packaged and installed with the surgical access port 110, with the lumen 540 inserted therethrough, and the surgical access port 110 may be snapped in place and operatively attached to the handle 520. Alternatively, the surgical access port 110 may be provided separately and placed onto the lumen 540 of the surgical instrument 500 by the user prior to inserting a distal end of the lumen 540, including the needle tip 550, of the instrument 500 into the patient's fascia, body wall, and/or body cavity. In one aspect, the lumen 540 and needle tip 550 may be in the form of the needle lumen 400 shown in FIGS. 14 and 15, and may be interchangeably attached to the handle 520. In one aspect, the surgical access port 110 may be attached to the surgical instrument 500 as shown in FIG. 15.

Figure 17:
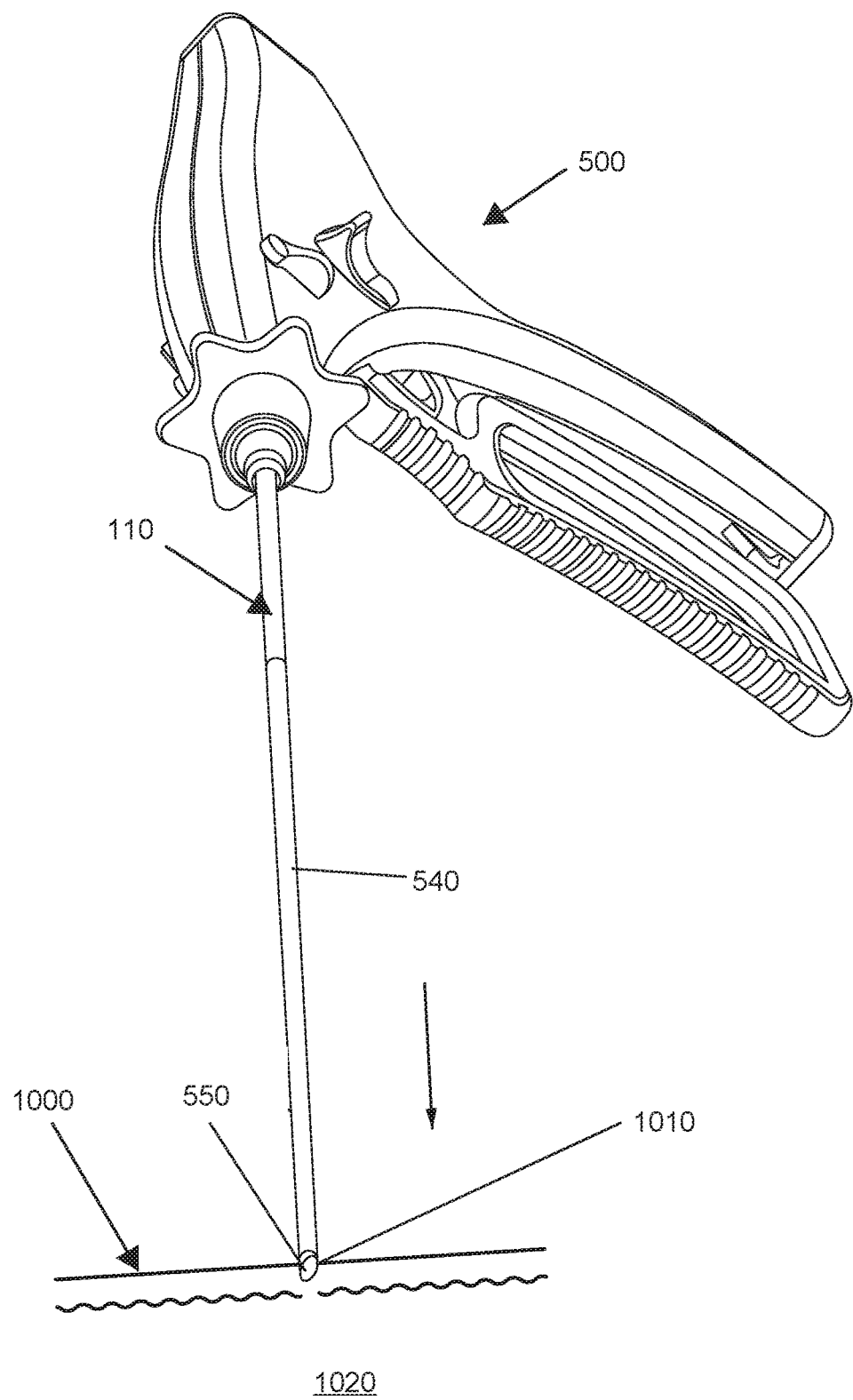
Figure 19:
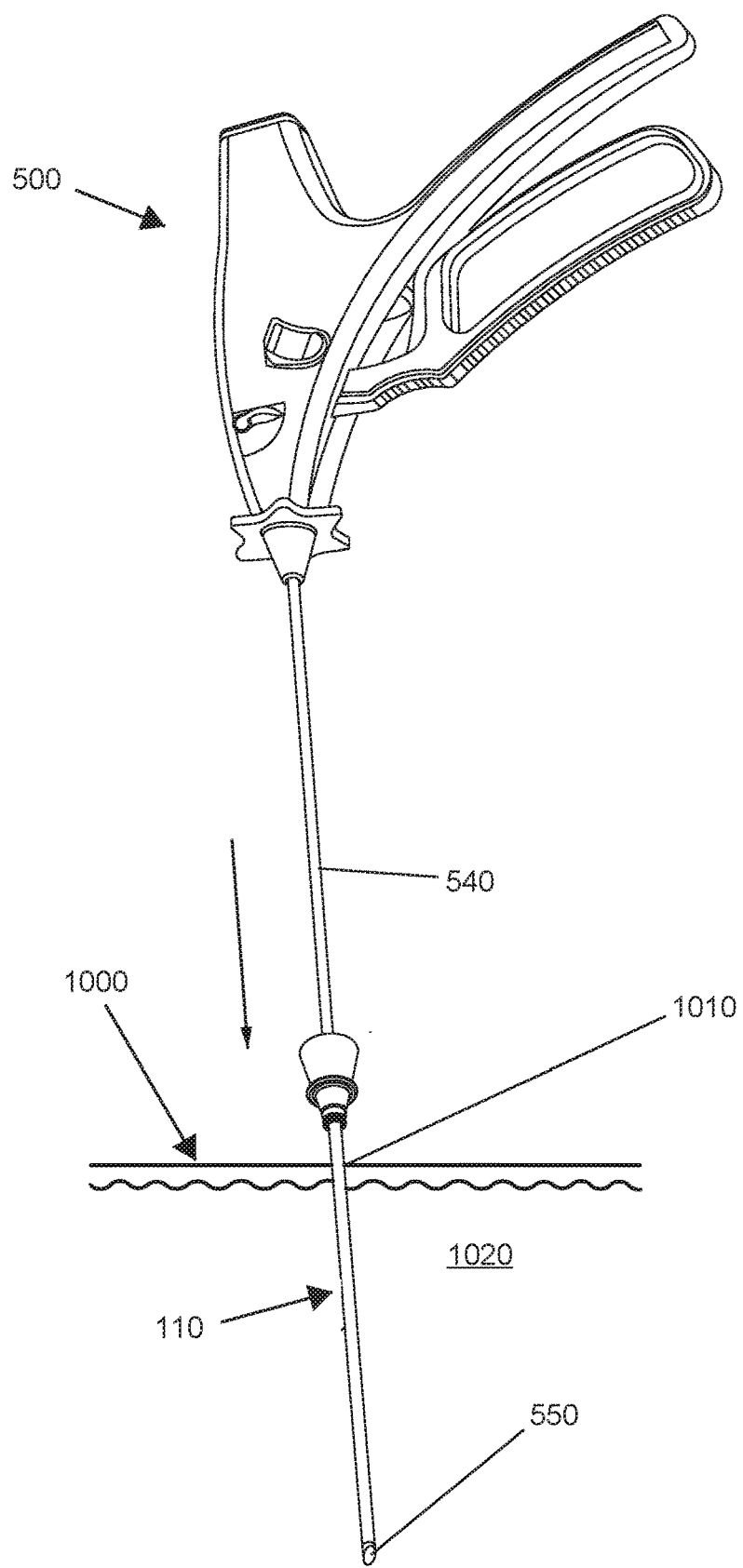
Figure 20:
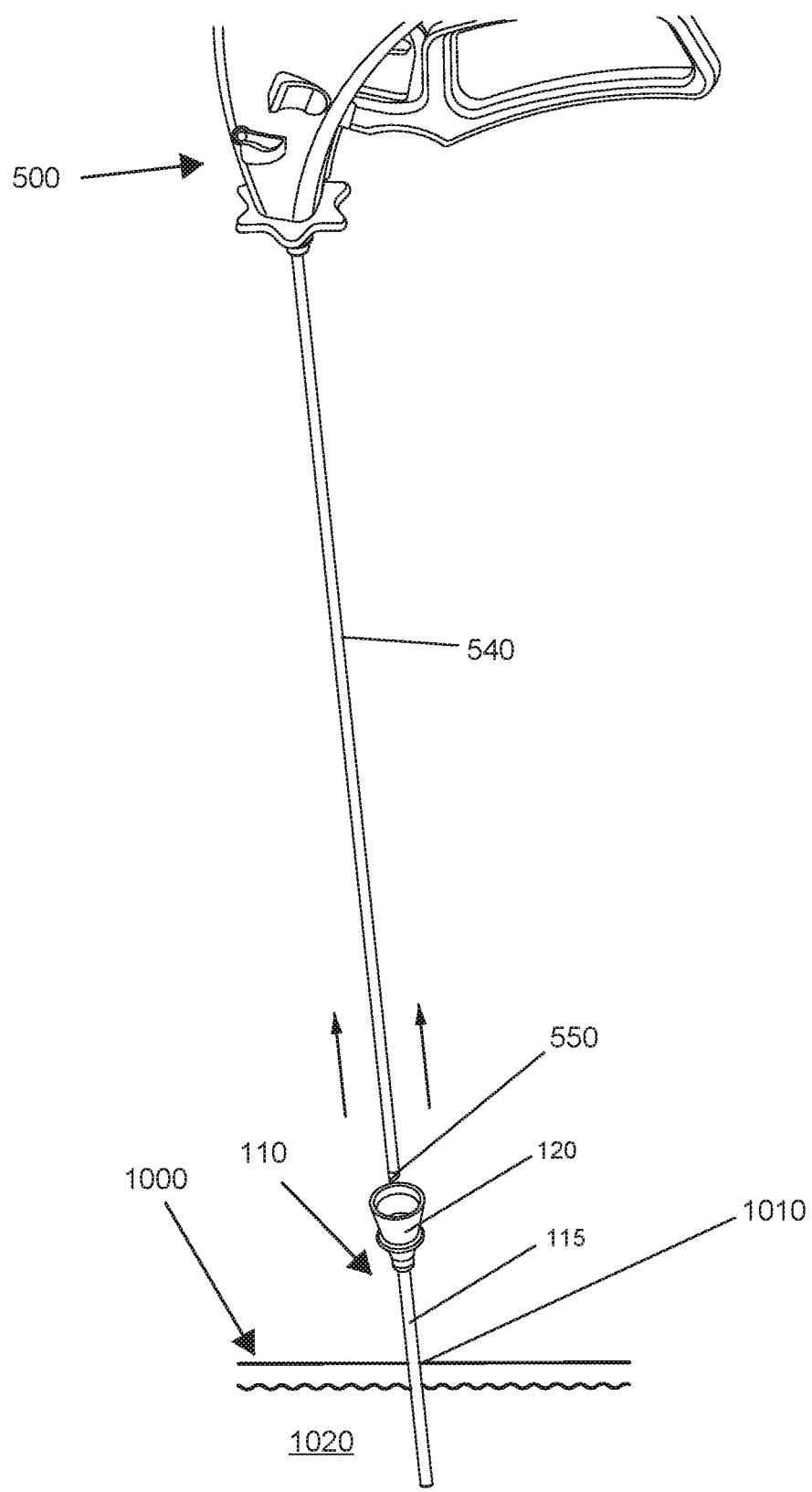
Figure 21:
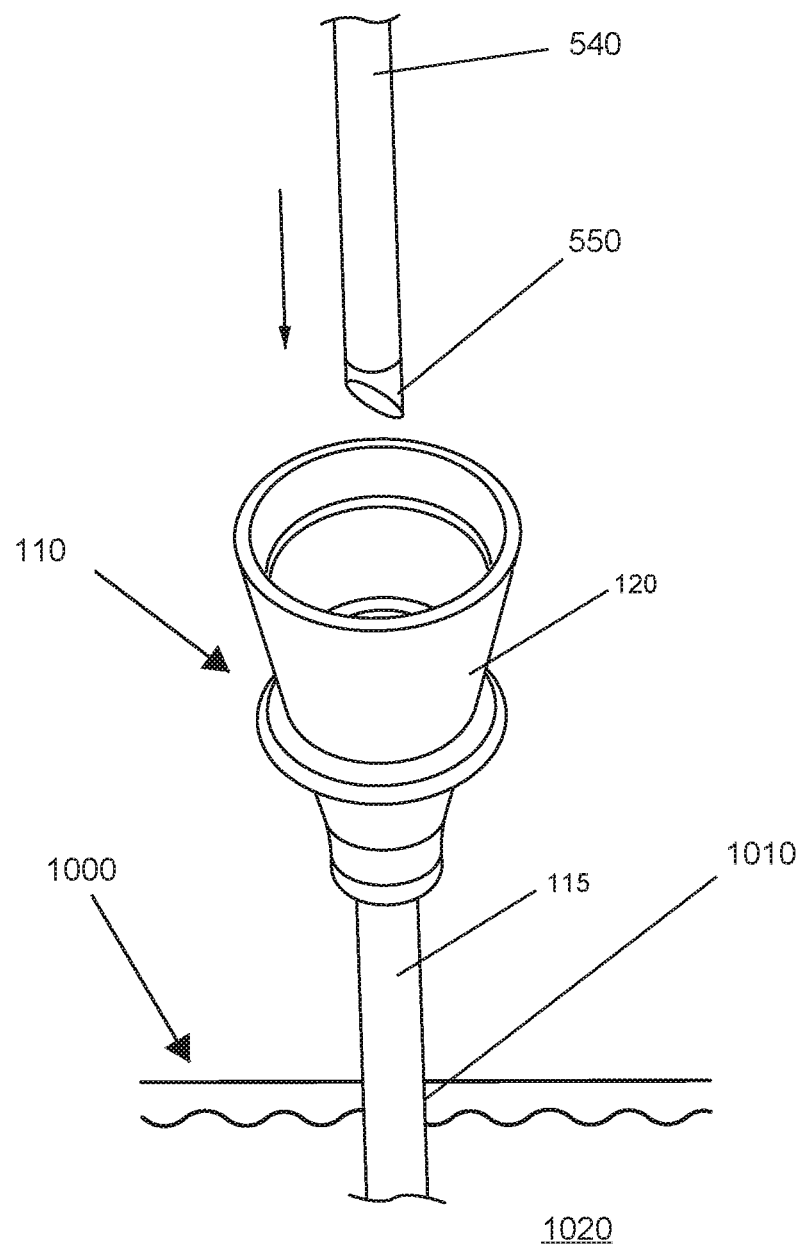
Figure 22:
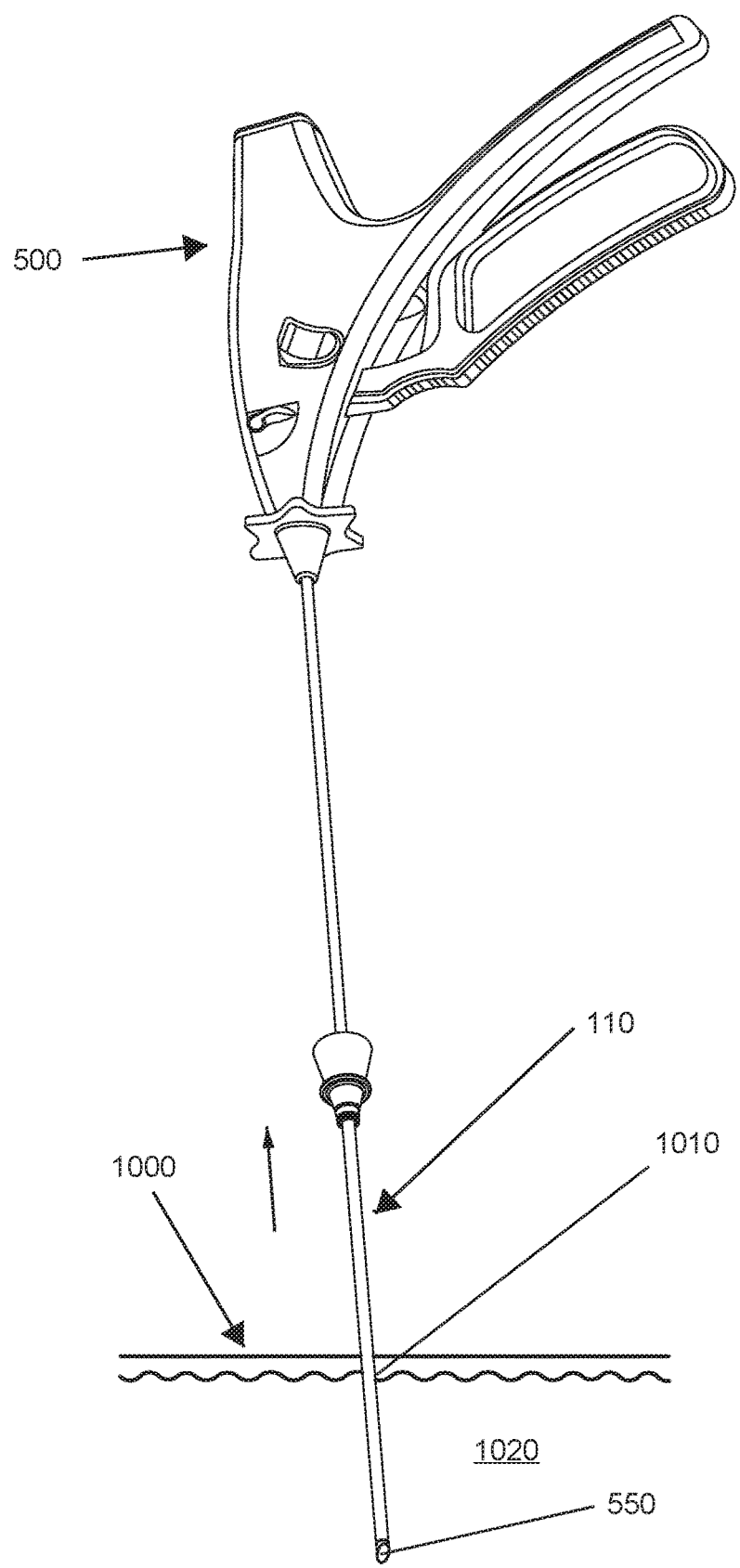
Figure 23:
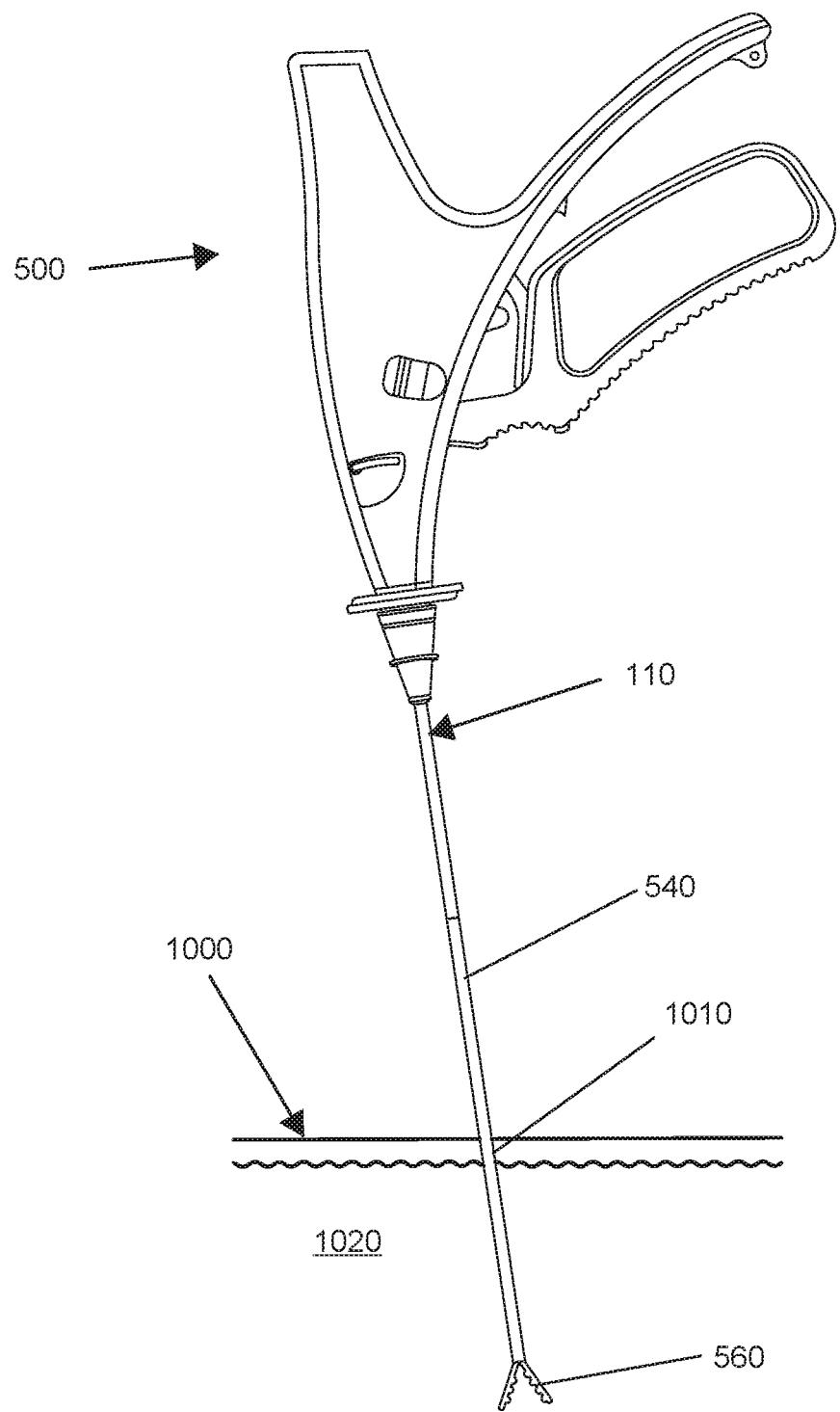
Figure 24:
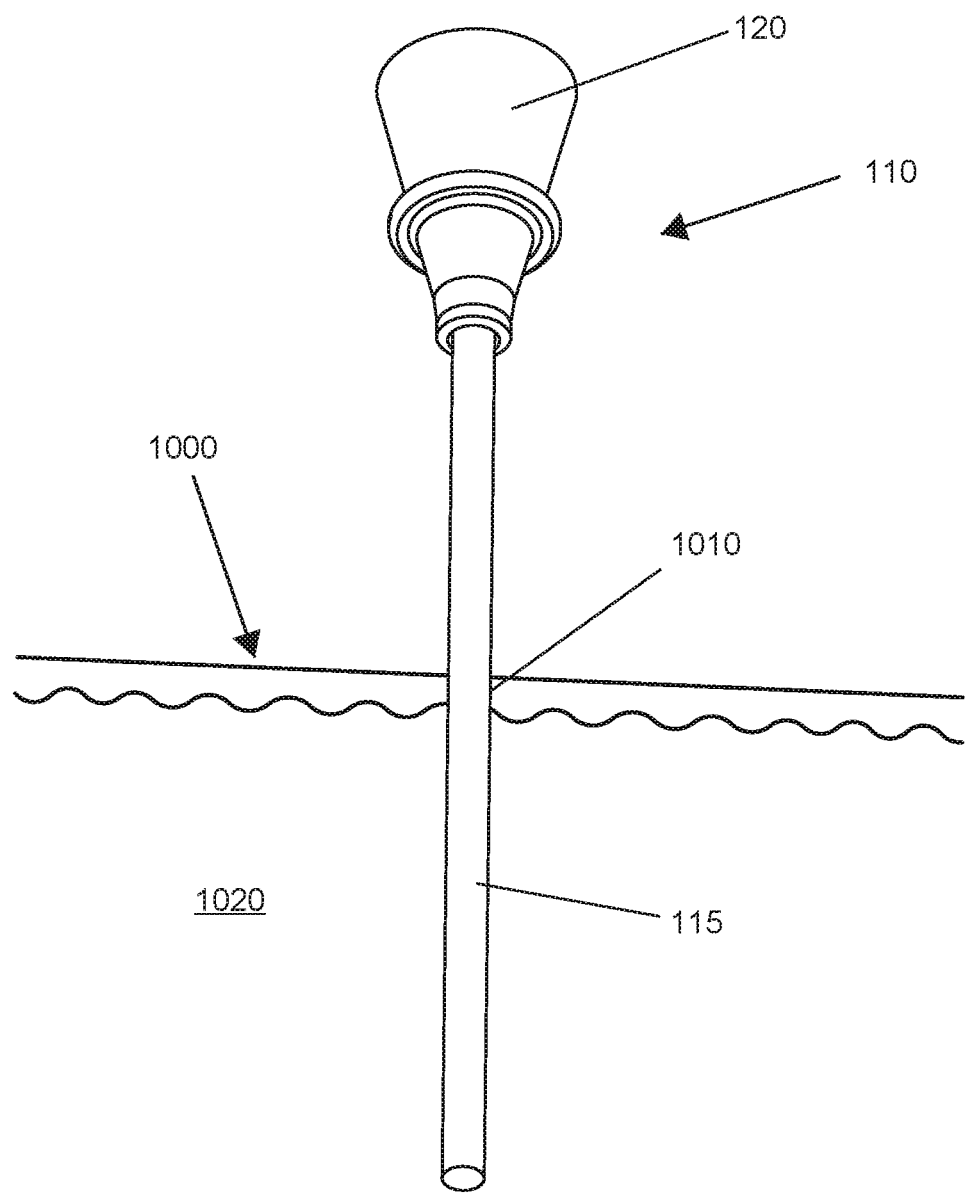

Next, as shown in FIGS. 17 and 19, the needle tip 550 of the surgical instrument 500 may be used to penetrate through a body wall 1000 of the patient, piercing a hole 1010 through the body wall 1000. In one aspect, the body wall 1000 may be a part of the abdominal wall of the patient. A length of the lumen 540 of the surgical instrument 500 may be inserted into a body cavity 1020 defined at least in part by the body wall 1000 of the patient. Once a length of the lumen 540 has been inserted into the body cavity, the surgical access port may be mounted to the body wall 1000 in order for other operative instruments to be later inserted into the same position, as will be described in further detail below.

In one aspect, once the lumen 540 has been inserted into the body cavity 1020, the surgical access port 110 may be slid down and advanced over the lumen 540, in a distal direction, towards the body cavity 1020, as shown in FIG. 19. The elongated cannula 115 of the surgical access port 110 may then be inserted through the hole 1010 generally created by the needle tip 550 and lumen 540 of the surgical instrument 500, as discussed above. In the process, the elongated cannula 115 may widen the hole 1010 created by the needle tip 550 and lumen 540.

The surgical access port 110 may then be further secured to the patient using the locking mechanism 300. The locking mechanism 300 may be pre-packaged and installed on the surgical instrument 500 together with the surgical access port 110. Alternatively, prior to the surgical instrument 500 being inserted into the patient, the locking mechanism 300 may be advanced over the lumen 540 of the surgical instrument, in a proximal direction. The locking mechanism 300 may then be further advanced over the elongated cannula 115 and locked to the surgical access port 110 by squeezing or pinching tabs 312A and 322A of the locking mechanism 300 together to place the device in a locked position. After the elongated cannula 115 of the surgical access port 110 has been inserted through the hole 1010, the adhesive portion of the base 310 may be secured onto the patient's fascia to secure the surgical access port 110 in place.

Figure 18:
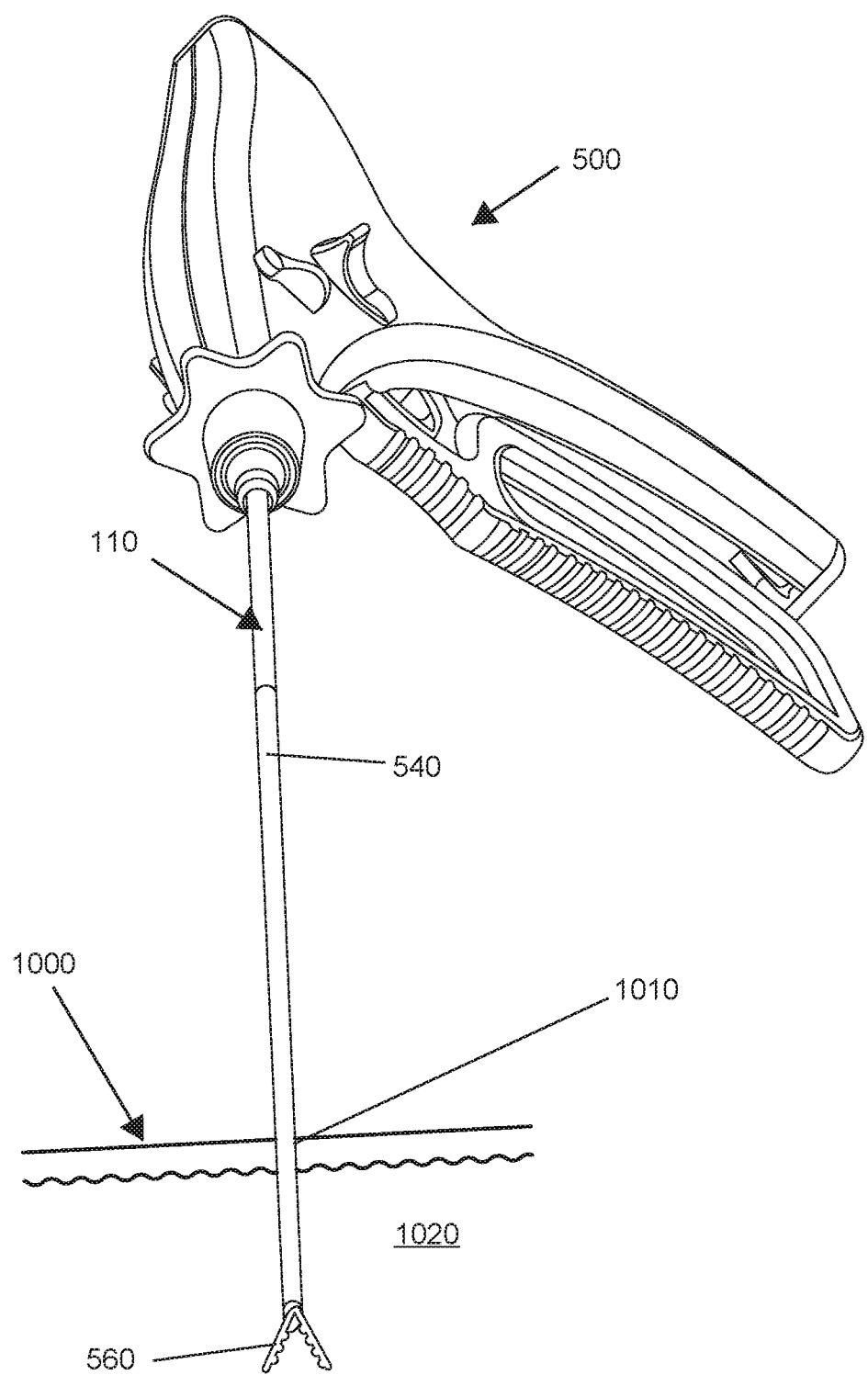

Referring to FIG. 18, in one aspect, the surgical instrument 500 may be operated within the body cavity 1020 prior to the surgical access port 110 being inserted into the hole 1010. For example, the surgical instrument 500 may include a pair of graspers 560 which may be used to perform a grasping function within the body cavity 1020 prior to and/or after the surgical access port 110 has been inserted into the hole 1010.

Referring to FIG. 19, once the surgical instrument 500 is no longer needed, the surgical access port 110 may be left in the body cavity 1020. In one aspect, the cap 150 (shown in FIG. 7) may be attached to the hub of the surgical access port 110 in order to seal the tapered open end portion 126 of the hub 120. When the surgical instrument 500 or other instruments need to be inserted into the body cavity 1020, the cap 150 may be removed and the surgical instrument 500 or other instruments may be inserted through the surgical access port 110. As will be appreciated by one skilled in the art in view of the present disclosure, a number of different instruments may access the body cavity 1020 via the surgical access port 110 throughout a surgery. Once the surgery is complete the surgical access port 110 may be removed manually by pulling the surgical access port 110 away from the body cavity 1020, or the surgical access port 110 may be slid back up the last instrument's shaft or lumen, snapped onto the back of said instrument's shaft and/or handle using the at least inner rings 118A, 118B, 118C of the surgical access port 110, and removed from the patient's body cavity, back through the body wall 1000 and out of the patient's fascia.

In one aspect, the surgical access port assembly 100 may be used after the surgeon has inserted an endoscope with a camera into a body cavity 1000, wherein the cavity 1000 may be subject to insufflation and/or distended. Using the endoscope and camera, the surgeon would locate a part of the patient's fascia for insertion of the surgical access port 110. The tip 130 of the surgical access port 110 may be removed to reveal the sharp tip 250 of the obturator 200. The surgeon would either create a small incision in the patient's fascia or use sufficient force to insert the surgical access port 110 via the sharp tip 250 at the distal end of the obturator 200. Once the surgical access port 110 has been inserted into the body cavity 1020, the obturator 200 may be removed. Either during the insertion step or after, the surgeon can adjust the angle of the surgical access port 110 via movement of the locking mechanism 300, more specifically via the movements of the ball 330. The locking mechanism 300 may be locked and also adhered to the patient's fascia via the adhesive on the lower portion of the base 310, with the surgeon removing the paper liner 340 via the tab 345. Once inserted, the distal end of the surgical access port 110 will be within the body cavity 1020 while the proximal end of the cannula 115 and the hub 120 extend out of the patient's fascia. The body cavity 1020 is therefore accessible for various surgical instruments.

Further advantages of the surgical access port assembly 100 of the present disclosure include retention of abdominal pressure during an abdominal surgery. Also the inventive device when in use during a surgery may be self-sealing without compromising insufflation pressure. While not being bound by theory, the inventors of the present application believe that dynamic friction between the outer edge of the small diameter cannula 115 and the patient's fascia and body wall result in minimal gas leakage during insufflation. Furthermore, in one aspect, control of an entry depth of the surgical access port 110 may be possible through retention and/or pivot of the locking mechanism 300. Thus, in use, the surgical access port assembly 100 of the present disclosure may enable a smaller diameter incision point, better angle and control for surgical instrument access into the body cavity, while still maintaining sufficient insufflation. The absence of a valve and sealing mechanism may result in lower friction which in turn may improve precision during the surgery. Such improved precision also reduces the surgical time and duration of the surgery which in turn improves surgical recovery by the patient and may reduce surgical complications and scarring.

Unlike typical trocars, the surgical access port 110 may be attached to the back end of the percutaneous instrument and may be slid down the shaft of the instrument into the patient's body to provide re-access to the same site location if the percutaneous instrument were to be removed or exchanged. While trocars are independently inserted in to the body cavity, the surgical access port 110 differs from typical trocars in that the surgical access port 110 may be slid into the body cavity over an instrument pre inserted into the body cavity.

In one aspect, the surgical access port 110 and the surgical instrument 500 may be packaged as a kit, whereby the surgical access port 110 is placed onto and snapped onto the lumen of the surgical instrument 500. It is also envisioned where the surgical access port 110 would be packaged separately, as a stand-alone product and may be attached to the surgical instrument 500 as needed.

The system and methods associated with the surgical access port includes improved surgical precision, reduced surgical time resulting in reduced trauma to the patient and possibly less scarring, reduced recovery time, less pain, easier handling of the device by the user via the locked rotational hub and multiple types of end-effectors, and other benefits.

It will be appreciated that the foregoing description provides examples of the surgical access port which may be used with a surgical instrument for minimally invasive surgery. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

The invention claimed is:

1. A locking mechanism for a surgical access port, the locking mechanism comprising:
 a lock base having a tab and an aperture configured to receive the surgical access port; and
 a locking member having a lock tab and an opening configured to receive the surgical access port,
 wherein the locking member is configured to rotate relative to the lock base into a locked position to secure the surgical access port when inserted into fascia, and
 wherein the locking member is configured to rotate relative to the lock base into an unlocked position when the tab and the lock tab are squeezed together.

2. The locking mechanism of claim 1, further comprising an adhesive on the lock base to secure the lock base to the fascia.

3. The locking mechanism of claim 1, further comprising a ball configured to fix a rotational orientation of the surgical access port in the locked position.

4. The locking mechanism of claim 3, wherein the ball has an opening configured to receive the surgical access port.

5. The locking mechanism of claim 3, wherein the ball is received between the lock base and the locking member.

6. The locking mechanism of claim 5, wherein the locking member is configured to compress the ball in the locked position.

7. The locking mechanism of claim 6, wherein the ball includes at least one slit that is compressed in the locked position.

8. The locking mechanism of claim 3, wherein the lock base has a frustoconical inner surface at least partially supporting the ball.

9. The locking mechanism of claim 1, wherein the lock base comprises a central ring defining at least one screw thread or ramp, and the locking member comprises at least one snap or finger received in the at least one screw thread or ramp to enable relative rotation.

10. A surgical access port assembly comprising:
  a surgical access port; and
  a locking mechanism comprising:
    a lock base having a tab and an aperture configured to receive the surgical access port; and
    a locking member having a lock tab and an opening configured to receive the surgical access port,
  wherein the locking member is configured to rotate relative to the lock base into a locked position to secure the surgical access port when inserted into fascia, and
  wherein the locking member is configured to rotate relative to the lock base into an unlocked position when the tab and the lock tab are squeezed together.

11. The surgical access port assembly of claim 10, wherein the locking mechanism further comprises an adhesive on the lock base to secure the lock base to the fascia.

12. The surgical access port assembly of claim 10, wherein the locking mechanism further comprises a ball configured to fix a rotational orientation of the surgical access port in the locked position.

13. The surgical access port assembly of claim 12, wherein the ball has an opening configured to receive the surgical access port.

14. The surgical access port assembly of claim 12, wherein the ball is received between the lock base and the locking member.

15. The surgical access port assembly of claim 14, wherein the locking member is configured to compress the ball in the locked position.

16. The surgical access port assembly of claim 15, wherein the ball includes at least one slit that is compressed in the locked position.

17. The surgical access port assembly of claim 12, wherein the lock base has a frustoconical inner surface at least partially supporting the ball.

18. The surgical access port assembly of claim 12, wherein the lock base comprises a central ring defining at least one screw thread or ramp, and the locking member comprises at least one snap or finger received in the at least one screw thread or ramp to enable relative rotation.

19. A method of securing a surgical access port to fascia with a locking mechanism having a lock base and a locking member, the method comprising:
  receiving the surgical access port in an aperture of the lock base and an opening of the locking member,
  inserting the surgical access port into the fascia; and
  rotating the locking member relative to the lock base into a locked position to secure the surgical access port; and
  rotating the locking member relative to the lock base into an unlocked position by squeezing together a tab of the lock base and a lock tab of the locking member to remove the surgical access port once surgery is complete.

* * * * *